United States Patent [19]

Cerini

[11] 3,961,046

[45] June 1, 1976

[54] MUMPS VACCINE AND PREPARATION THEREOF

[75] Inventor: Costantino Peter Cerini, Pearl River, N.Y.

[73] Assignee: American Cyanamid Company, Stamford, Conn.

[22] Filed: Dec. 2, 1974

[21] Appl. No.: 528,752

[52] U.S. Cl. .................................. 424/89; 195/1.3
[51] Int. Cl.² .................. A61K 39/12; C12K 5/00; C12K 7/00
[58] Field of Search .................. 195/1.3; 424/89

[56] References Cited
UNITED STATES PATENTS 3,555,149  1/1971  Buynak et al. .................. 195/1.3
3,829,361  8/1974  Hoshino et al. .................. 195/1.3

*Primary Examiner*—Sam Rosen
*Attorney, Agent, or Firm*—Jack W. Richards

[57] ABSTRACT

A non-pathogenic but antigenic live mumps virus useful in making mumps vaccine is produced by three serial passages through primary human amnion cell monolayers followed by one passage in embryonated chicken eggs and finally by from 8 through 28 serial passages in primary chick embryo tissue cells.

7 Claims, No Drawings

MUMPS VACCINE AND PREPARATION THEREOF

BACKGROUND OF THE INVENTION

This invention relates to vaccines and particularly to an attenuated, live mumps virus which is to be injected into human beings to protect them against mumps.

This invention concerns a live non-pathogenic attenuated mumps virus and its use as a vaccine which after injection into humans will confer protection against mumps. The clinical features of mumps infection are well documented. The disease is one of childhood and it confers durable immunity. Adults who have escaped childhood exposure can be infected in later life. Any detectable level of antibody is considered protective in man. The attenuated live mumps virus stimulates formation of antibody in humans with no production of clinical illness.

Mumps vaccines and their preparations are, of course, known. U.S. Pat. No. 3,555,149 discloses a live attenuated mumps virus vaccine prepared by growing the virus in at least 10 successive passages in embryonated hens' eggs followed by propagation in chick embryo tissue culture. In contrast thereto, the present invention prepares live mumps virus by growing the virus in three serial passages through primary human amnion tissue cell monolayers followed by one passage in embryonated chicken eggs and by from 8 through 28 serial passages in primary chick embryo tissue cells.

SUMMARY OF THE INVENTION

In general, the preparation of the live mumps virus vaccine of the invention involves the following steps:

A. the isolation of the virulent virus in primary human amnion cell monolayers, replication in embryonated chicken eggs and adaptation to chick embryo tissue culture; (B) development of the attenuated virus by serial passages in chick embryo tissue culture; and (C) preparation of the vaccine from this attenuated live virus.

In the present invention, live mumps virus is prepared by growing the virus in three successive passages in primary human amnion tissue culture, followed by one passage in embryonated hens' egg and from 8 through 28 serial passages in chick embryo tissue culture. The mumps virus is isolated from clinical material in primary human amnion tissue culture. After three serial passages it is adapted to chick tissue by one passage in embryonated hens' eggs. The virus was successfully passaged in primary human amnion tissue culture, embryonated hens' egg and chick embryo tissue cultures to adapt, replicate and attenuate. The above passages have been performed using both undiluted and dilute inocula and were harvested only once.

More specifically, each step in the preparation of the live mumps vaccine of the invention may be described as follows:

A. The live mumps virus may be obtained from humans having an active mumps infection. This virus is inoculated into primary human amnion (PHA) cell monolayers and incubated at 34°C. 37°C. (preferably 36°C.) for 7 to 12 days (preferably 10 days). This virus is harvested and inoculated into PHA cells a second time under the same conditions for 7 to 12 days (preferably 7 days). This harvest is inoculated into PHA cells a third time, incubated under the same conditions for 7 to 12 days (preferably 11 days) and again harvested as before. This harvest is inoculated into the amnion of 6 days old embryonated chicken eggs and incubated as above for 6 to 8 days (preferably 7 days). The harvest was inoculated into primary chick embryo fibroblast cells (CETC) incubated as above for 6 to 8 days (preferably 7 days) and harvested.

B. This harvest is inoculated undiluted into CETC, incubated from 32° to 37°C. for 4 to 13 days (preferably 7 days) and harvested by freezing. This passage in CETC is repeated 9 to 27 times employing either an undiluted harvest or a harvest diluted from $10^{-1}$ to $10^{-3}$.

C. The mumps virus harvested after repeated serial passages in CETC is non-pathogenic, causes no clinical illness in humans and invokes detectable level of antibody. The virus infectivity is stabilized by the addition of a suitable stabilizer which may be sucrose, human albumin, glutamine, phosphate, sorbitol, sorbitol and N-Z amine NaK or mixture of stabilizers. The virus pool is stored frozen. Thawed aliquots are filled into vials, freeze-dried and stored at 4°C. for use.

DETAILED DESCRIPTION OF THE INVENTION

The invention will be illustrated in more detail by the following representative examples.

EXAMPLE 1

Propagation of Mumps Virus in Primary Human Amnion Cell Monolayers for Three Passages Saliva swabs obtained from a child having an uncomplicated case of mumps are pooled and inoculated into plastic bottles containing primary human amnion (PHA) cell monolayers. The bottles are incubated at 36°C. for 10 days and then harvested by freezing tissue culture cells and fluid together. This harvest is inoculated undiluted into PHA cells a second time, incubated for 7 days at 36°C. and harvested as before. This second harvest is inoculated undiluted into PHA cells a third time, incubated for 11 days at 36°C. and harvested as before.

EXAMPLE 2

Propagation of Mumps Virus from Primary Human Amnion Cell into Embryonated Chicken Eggs for One Passage The harvest from Example 1 is inoculated undiluted into the amnion of six days old embryonated hens' eggs. After 7 days incubation at 36°C. the amniotic fluid is harvested and pooled.

EXAMPLE 3

Propagation of Mumps Virus from Embryonated Chicken Eggs Into Chick Embryo Fibroblast Cells for Multiple Passages The amniotic fluid harvest from Example 2 is inoculated undiluted into glass bottles containing a primary monolayer of chick embryo fibroblast cells (CETC), incubated for 7 days at 36°C. and then harvested by freezing tissue culture cells and fluid together. This harvest is inoculated undiluted into CETC monolayers, incubated for 7 at 36°C. and again harvested by freezing. This second harvest is inoculated undiluted into CETC monolayers, incubated for 10 days at 36°C. and harvested by freezing. This third harvest is inoculated at a $10^{-2}$ dilution into CETC monolayers, incubated for 8 days at 36°C. and harvested by freezing. This fourth harvest is inoculated at a $10^{-2}$ dilution into a cell suspension of CETC, mixed for 2 hours, planted in glass bottles, incubated for 13 days at 36°C. and harvested by freezing. This fifth harvest is inoculated at a $10^{-1}$ dilution into a cell suspension of CETC, mixed for 2 hours, planted in glass bottles, incubated for 4 days at 36°C. and harvested by freezing. This sixth harvest is inoculated at a $10^{-2}$ dilution into a suspension of CETC, mixed for 2 hours, planted in glass bottles, incubated for 4 days at 36°C. and harvested by freezing. This seventh harvest is inoculated at a $10^{-3}$ dilution into a suspension of CETC, mixed for 2 hours, planted in glass bottles, incubated for 7 days at 36°C. and harvested.

Thus the virus in this harvest has had 3 PHA passages (Example 1) 1 egg passage (Example 2) and 8 CETC passages (Example 3).

EXAMPLE 4

Preparation of Vaccine from Attenuated Mumps Virus

A suspension of chick fibroblast cells at a concentration of 2,000,000 viable cells per milliliter in Eagle's Basal Medium (BME) with 10% inactivated calf serum is inoculated with an appropriate dilution of the eighth and final harvest of Example 3. The mixture is incubated 1–2 hours at room temperature and then planted into glass bottles and incubated at 36°C. At 24 hours after inoculation the growth medium is decanted aseptically and the bottle cultures are washed twice with 100 ml. portions of phosphate buffered saline. A 100 ml. portion of BME maintenance medium is added to each bottle culture and the bottles are incubated for 6 days at 36°C. On the 7th day after inoculation a single harvest is collected by removing and pooling the maintenance medium. The harvest is filtered through a 5 micron Millipore membrane. The virus infectivity is stabilized by the addition of a stabilizer to a final concentration of 4% N-Z amine and 4% sorbitol. The virus is then frozen in a dry-ice-alcohol mix and stored at −60°C. Infectivity titrations are performed in CETC. The virus stabilized harvest is thawed, diluted to an appropriate level based on infectivity titers, distributed into vials, freeze-dried and stored at 4°C.

EXAMPLE 5

Further Propagation of Mumps Virus in CETC

The virus may be further propagated as follows:
The eighth and final harvest from Example 3 is inoculated at a $10^{-3}$ dilution in a suspension of CETC, mixed for 2 hours, planted in glass bottles, incubated for 7 days at 36°C. and harvested by freezing.

Further propagation in abbreviated form is as follows:

| Harvest | Inoculation Strength in CETC | Incubation at 36°C. | Harvest |
|---|---|---|---|
| 9th | $10^{-4}$ Dilution | 7 days | 10th |
| 10th | $10^{-3}$ Dilution | 6 days | 11th |
| 11th | $10^{-3}$ Dilution | 7 days | 12th |
| 27th plus | $10^{-3}$ Dilution | 7 days | 28th plus |

The final harvest is processed into a vaccine as described in Example 4.

I claim:
1. A mumps vaccine comprising:
A. as its essential ingredient an immunologically effective amount of an attenuated mumps virus characterized by
   a. when injected into humans
      i. being free of clinical manifestatins of the disease and
      ii. invoking in man an antibody response to a virulent virus;
   b. being capable of inducing its own replication in living cells; and
   c. having been attenuated from virulent mumps virus by three serial passages in primary human amnionic cell monolayers at 34°C. to 37°C., followed by one passage in embryonated chicken eggs at 34°C. to 37°C., followed by replication in chick embryo tissue at 32°C. to 37°C. for from 8 through 28 passages; and
B. a stabilizer.

2. A vaccine of claim 1 wherein the stabilizer is sorbitol and N-Z amine NaK.

3. A freeze-dried mumps vaccine of claim 1.

4. A mumps vaccine comprising:
A. as its essential ingredient an immunologically effective amount of an attenuated mumps virus characterized by
   a. when injected into humans
      i. being free of clinical manifestations of the disease, and
      ii. invoking in man an antibody response to a virulent virus;
   b. being capable of inducing its own replication in living cells; and
   c. having been attenuated from virulent mumps virus by three serial passages in primary human amnionic cell monolayers at 36°C., followed by one passage in embryonated chicken eggs at 36°C., followed by replication in chick embryo tissue at 36°C. for from 8 through 23 passages; and
B. sorbitol and N-Z amine NaK as stabilizer.

5. A freeze-dried mumps vaccine of claim 4.

6. A process of preparing a live mumps virus useful as an antigen in a vaccine which will evoke in man an antibody response against a virulent mumps virus without causing the severe clinical manifestations of the disease which comprises growing the virulent virus by three serial passages in primary human amnionic cell monolayers at 34°C. to 37°C., followed by one passage in embryonated chicken eggs at 34°C. to 37°C., followed by replication in chick embryo tissue at 32°C. to 37°C. for from 8 through 28 passages.

7. A process of preparing a live mumps virus useful as an antigen in a vaccine which will evoke in man an antibody response against a virulent mumps virus without causing clinical manifestations of the disease which comprises growing the virulent virus by three serial passages in primary human amnionic cell monolayers at 36°C., followed by one passage in embryonated chicken eggs at 36°C., followed by replication in chick embryo tissue at 36°C. for from 8 through 23 passages.

* * * * *